(12) United States Patent
Ding et al.

(10) Patent No.: US 8,858,792 B2
(45) Date of Patent: Oct. 14, 2014

(54) HEMODIALYSIS AND PERITONEAL DIALYSIS SYSTEMS HAVING ELECTRODEIONIZATION CAPABILITIES

(75) Inventors: Yuanpang Samuel Ding, Libertyville, IL (US); Ying-Cheng Lo, Green Oak, IL (US); Joshua James Miller, Wilmette, IL (US); Justin Rohde, Des Plaines, IL (US); Sujatha Karoor, Lake Forest, IL (US); Stephane Dupont, Elancourt (FR)

(73) Assignees: Baxter International Inc., Deerfield, IL (US); Baxter Healthcare S.A., Glattpark (Opfikon) (CH); EMD Millipore Corporation, Billerica, MA (US)

( * ) Notice: Subject to any disclaimer, the term of this patent is extended or adjusted under 35 U.S.C. 154(b) by 522 days.

(21) Appl. No.: 12/718,609

(22) Filed: Mar. 5, 2010

(65) Prior Publication Data

US 2010/0224492 A1 Sep. 9, 2010

Related U.S. Application Data

(60) Provisional application No. 61/158,101, filed on Mar. 6, 2009.

(51) Int. Cl.
| | |
|---|---|
| *B01D 61/26* | (2006.01) |
| *B01D 61/44* | (2006.01) |
| *B01D 61/48* | (2006.01) |
| *A61M 1/14* | (2006.01) |
| *A61M 1/16* | (2006.01) |
| *A61M 1/28* | (2006.01) |

(52) U.S. Cl.
CPC ......... *A61M 1/1696* (2013.01); *A61M 1/1674* (2014.02); *A61M 1/287* (2013.01)
USPC ........ 210/195.2; 210/200; 210/252; 210/263; 210/294; 210/295; 210/321.6; 210/501; 210/502.1

(58) Field of Classification Search
USPC ......... 210/748.1, 748.11, 200, 252, 263, 294, 210/295, 321.6, 501, 502.1, 195.1, 195.2; 204/535, 630, 632, 628, 637, 540, 536, 204/539; 604/6.08, 6.09, 29
See application file for complete search history.

(56) References Cited

U.S. PATENT DOCUMENTS

| | | | |
|---|---|---|---|
| 5,244,568 | A | 9/1993 | Lindsay et al. |
| 5,350,357 | A | 9/1994 | Kamen et al. |
| 5,585,003 | A | 12/1996 | Van Newenhizen |

(Continued)

FOREIGN PATENT DOCUMENTS

| | | |
|---|---|---|
| WO | 03/040042 | 5/2003 |
| WO | 2010/024963 | 3/2010 |

OTHER PUBLICATIONS

International Preliminary Report on Patentability for International Application No. PCT/US2010/026336 mailed on Aug. 5, 2011.

(Continued)

*Primary Examiner* — John Kim
(74) *Attorney, Agent, or Firm* — K&L Gates LLP

(57) ABSTRACT

Systems and methods for hemodialysis or peritoneal dialysis having integrated electrodeionization capabilities are provided. In an embodiment, the dialysis system includes a carbon source, a urease source and an electrodeionization unit. The carbon source and urease source can be in the form of removable cartridges.

22 Claims, 4 Drawing Sheets

(56) References Cited

U.S. PATENT DOCUMENTS

| | | |
|---|---|---|
| 5,662,806 A | 9/1997 | Keshaviah et al. |
| 5,873,853 A | 2/1999 | Keilman et al. |
| 5,984,891 A | 11/1999 | Keilman et al. |
| 6,187,162 B1 * | 2/2001 | Mir .............................. 204/524 |
| 6,196,992 B1 | 3/2001 | Keilman et al. |
| 6,592,542 B2 | 7/2003 | Childers et al. |
| 7,318,892 B2 | 1/2008 | Connell et al. |
| 2003/0105424 A1 | 6/2003 | Karoor et al. |
| 2007/0179431 A1 | 8/2007 | Roberts et al. |

OTHER PUBLICATIONS

International Search Report, PCT/US2010/026336 mailed Jul. 26, 2010, 6 pages.

Written Opinion, PCT/US2010/026336 mailed Jul. 26, 2010, 9 pages.

* cited by examiner

HEMODIALYSIS AND PERITONEAL DIALYSIS SYSTEMS HAVING ELECTRODEIONIZATION CAPABILITIES

PRIORITY CLAIM

This application claims priority to and the benefit of U.S. Provisional Patent Application No. 61/158,101, filed Mar. 6, 2009, the entire content of which is expressly incorporated herein by reference.

JOINT RESEARCH AGREEMENT

The claimed invention was made as a result of activities undertaken within the scope of a joint research agreement as defined under 35 U.S.C. 103(c) between Baxter International Inc. and Millipore Corporation. The joint research agreement was in effect on or before the date the claimed invention was made.

BACKGROUND

The present disclosure generally relates to dialysis systems. More specifically, the present disclosure relates to systems and methods for hemodialysis or peritoneal dialysis that recycle used dialysate through an electrodeionization based regeneration system. These systems can perform high volume dialysis treatments without using large volumes of fresh dialysis fluid.

In both hemodialysis and peritoneal dialysis, two general classes of dialysis systems currently exist. The first class uses fresh fluid (e.g., from a solution bag or some sort of water purification system) to generate dialysis fluid that is used to dialyze the individual. The second class uses "sorbent" technology to remove uremic toxins from waste dialysate. Therapeutic agents such as ions and/or glucose can be injected into the treated dialysate, which is used to continue the dialysis of the individual. The main advantage of the sorbent based approach is that very low volumes of fluid are required to achieve high volume dialysis treatments.

Disadvantages of sorbent systems include their high cost, disposability, and concerns regarding the purity of the recycled solution, as many ions remain in the fluid after treatment and verification of purity is technically challenging to perform. For example, sorbents can have high cartridge costs, insufficient removal of all of the tap water impurities, and insufficient removal of all of the uremic toxins in the used dialysate (e.g., sulfate). In addition, possible chemicals may be released or leached from the sorbent cartridge (e.g., zirconium). There may also be potential issues with pH and sodium balance.

SUMMARY

The present disclosure relates to systems and methods for hemodialysis or peritoneal dialysis having integrated electrodeionization ("EDI") capabilities. The EDI systems and methods can further be utilized in portable dialysis devices such as wearable artificial kidneys. In a general embodiment, the dialysis system includes a carbon source, a urease source, and an EDI unit. The carbon source and urease source can be in the form of removable cartridges. The EDI approach maintains the advantage of low fluid use in a sorbent system, but addresses the key shortcomings of the sorbent system. The EDI technology is re-usable over very long periods of time (e.g., 5-7 years) thereby reducing cost, and essentially removes all ionic contaminants from the waste dialysate (not just selective ions), resulting in verifiably pure recycled solution.

In another embodiment, the disclosure provides a method of performing hemodialysis. The method comprises passing a spent dialysis fluid from a dialyzer through a carbon source, a urease source and an electrodeionization unit to produce a clean dialysis fluid, and passing the clean dialysis fluid through the dialyzer. The clean dialysis fluid can pass through an ion exchange unit before passing through the dialyzer. In addition, one or more dialysis components can be added to the clean dialysis fluid before the clean dialysis fluid passes through the dialyzer.

In an alternative embodiment, the present disclosure provides a method of performing peritoneal dialysis. The method comprises passing a spent dialysis fluid from an individual through a carbon source, a urease source and an electrodeionization unit to produce a clean dialysis fluid, and returning the clean dialysis fluid to the individual. The clean dialysis fluid can pass through an ion exchange unit before returning to the patient. One or more dialysis components can be added to the clean dialysis fluid before returning to the individual. The clean dialysis fluid can also pass through a filter or an ultraviolet bactericidal light returning to the patient.

In yet another embodiment, the present disclosure provides a method of performing dialysis. The method comprises passing a spent dialysis fluid through a dialysis compartment of a dialyzer including an ion-rejection membrane that allows the passage of negatively charged ions and nonionic species but restricts the passage of positively charged ions. The ion-rejection membrane separates the dialysis compartment from a dialysate compartment of the dialyzer. The method further comprises passing used dialysis fluid generated from the dialysate compartment of the dialyzer through a carbon source, a urease source and an EDI unit to produce a clean dialysis fluid. A source containing any desired negative ions is then added to the clean dialysis fluid. The clean dialysis fluid passes through the dialysate compartment of the dialyzer.

In an alternative embodiment, the ion-rejection membrane allows the passage of positively charged ions and nonionic species but restricts the passage of negatively charged ions. In this regard, a source containing any desired positive ions is then added to the clean dialysis fluid.

An advantage of the present disclosure is to provide an improved hemodialysis system.

Another advantage of the present disclosure is to provide an improved peritoneal dialysis system.

Yet another advantage of the present disclosure is to provide a dialysis system that has a high purity of recycled dialysis fluid.

Still another advantage of the present disclosure a dialysis system having low operating costs.

Additional features and advantages are described herein, and will be apparent from, the following Detailed Description and the figures.

DETAILED DESCRIPTION

The present disclosure relates to systems and methods for hemodialysis or peritoneal dialysis having integrated EDI capabilities. In alternative embodiments, the EDI systems and methods can be utilized and implemented in various hemodialysis and peritoneal dialysis technologies. Such dialysis systems are described in U.S. Pat. Nos. 5,244,568, 5,350,357, 5,662,806, 6,592,542 and 7,318,892, which are incorporated herein by reference. The EDI systems and methods can further be utilized in portable dialysis devices such as, for example, wearable artificial kidneys in which an individual may move freely during dialysis. Portable dialysis devices are described in U.S. Pat. Nos. 6,196,992, 5,873,853 and 5,984,891, which are incorporated herein by reference. The EDI systems and methods can be used in medical centers and be implemented with on-site or at-home dialysis treatments.

It should be appreciated that the EDI systems discussed herein differ from electrodialyzers. There are major differences between electrodialysis and EDI. An electrodialyzer is used to remove electrolytes from an aqueous feed solution introduced into a diluate chamber. An example of an electrolyte is NaCl. However, the level of electrolyte removal is not allowed to go below a certain limit. If one goes to a lower limit with very few electrolyte-based ions left in the solution, water splitting occur (also known as "electrolysis"), and a considerable amount of energy is wasted in splitting the water. This water splitting is needed for the current to flow between the electrodes maintained in the elctrodialysis stack. The proton and the hydroxyl ion resulting from the water splitting will carry the current. It is to be avoided for a variety of reasons.

Figure 1:
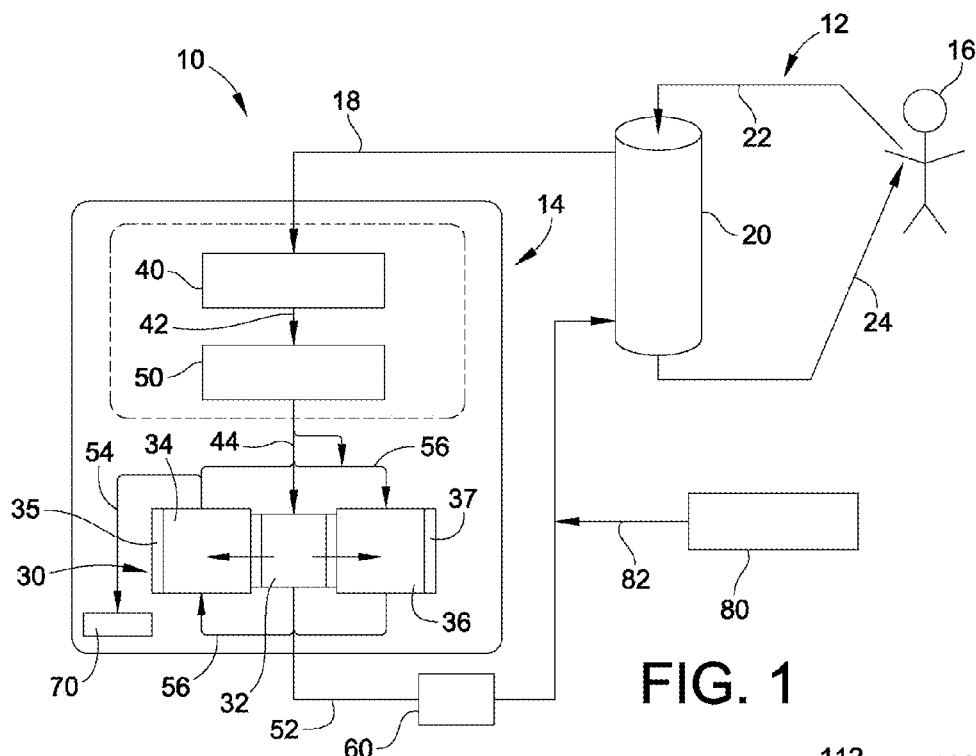
FIG. 1 illustrates a schematic of a dialysis fluid recycling system for hemodialysis in an embodiment of the present disclosure.

An electrodeionizer is an electrodialyzer in which the diluate channel into which the feed solution is introduced is filled with a bed of mixed ion exchange resin beads. At the top of the channel where the feed solution is introduced, the electrolytes present in the feed solution carry the current. Even though the ion exchange resin beads are there, they do not serve much of a deionization function. The mixed ion exchange resin beads in the electrodeionizer enhance the efficiency of removing the electrolytes from the dialysate solution as well as alleviate the effects of water splitting as a result of little to no electrolytes remaining in the solution further down the channel In a general embodiment, a dialysis fluid recycling system 10 for hemodialysis is illustrated in FIG. 1. As shown in FIG. 1, a circuit 12 represents a standard blood circuit for a hemodialysis machine. Circuit 12 cycles blood from an individual 16 via flow path 22 through a dialyzer 20 and returns it to the individual's body via flow path 24. Dialyzer 20 can include a dialysate compartment and a blood compartment separated by a suitable membrane. A circuit 14 includes an EDI unit or module 30 in dialysis fluid recycling system 10. Circuit 14 can also include a carbon source 40 and a urease source 50 connected to carbon source 40 via flow path 42. Carbon source 40 and urease source 50 can be in the form of removable cartridges.

EDI unit 30 can include a central chamber 32, an anion chamber 34 having an anode 35, and a cation chamber 36 having a cathode 37. As fluid exiting urease source 50 flows to central chamber 32 via flow path 44, a potential difference between anode 35 and cathode 37 causes the electrolytes in the fluid in central chamber 32 to flow into anion chamber 34 and cation chamber 36. Specifically, negatively charged ions flow into anion chamber 34 while positively charged ions flow into cation chamber 36 where they are subsequently removed. The treated fluid that passes through EDI unit 30 exits as part of a treated fluid stream via flow path 52. A waste fluid stream filled with electrolytes exits via flow path 54 that can lead to a drain 70.

EDI unit 30 can also be modified so that a suitable quantity of fluid can be recirculated around EDI unit 30 via flow path 56. This reduces the amount of fluid flowing through EDI unit 30 that would end up as part of the waste fluid stream. As a result, a higher quantity of fluid exits as the treated fluid stream as compared to the quantity of treated fluid from an EDI unit without recirculation.

During operation, after priming system 10 with an appropriate amount of fluid (in this case, priming fluid can be any of, dialysis fluid, sterile bagged water, tap water in its raw form, tap water purified through standard means such as deionization and/or reverse osmosis, or a combination therein), the dialysis solution is recirculated through circuit 14 via flow path 18 in the direction indicated. Used dialysis fluid leaves dialyzer 20 saturated with uremic toxins, as well as normal dialysis fluid components such as dextrose and ions (e.g., sodium, calcium, magnesium, etc.). The organic toxins of the fluid, as well as the lactate or bicarbonate buffer of the solution, are then removed from the fluid through adsorption onto a carbon surface (e.g. activated carbon or other appropriate organic neutralizing surface) of carbon source 40.

Urea, which is not well removed by carbon, is then exposed to urease source 50. Urease is an enzymatic catalyst which facilitates the breakdown of urea into ammonium and ammonia (e.g., depending on pH). Urease source 50 can be immobilized on any suitable surface that allows the passage of a liquid or be a membrane impregnated with cross-linked urease enzyme crystals.

The pKa of ammonium ion is 9.25. For efficient removal, the pH needs to be below neutral. At lower pH's, a greater portion of ammonia will be in ionized form. Passing it through an optional cation exchanger will help lower the pH and have better removal of ammonia. Removal of the ammonium in can also be accomplished within EDI unit 20.

After the fluid has passed through urease source 50, all organic contaminants will have been adsorbed or broken down into ionic contaminants before entering EDI unit 30. In EDI unit 30, ions are removed from the fluid through electromagnetic facilitated transport through cation and anion selective membranes. The fluid that exits EDI unit 30, in contrast to currently existing sorbent systems, contains very few ions, e.g., with nominal fluid resistivity approaching or in excess of 5 MΩ·cm. In this regard, EDI unit 30 can render the zirconium phosphate layer, zirconium bicarbonate layer and/or ion exchange layer typically used for ammonium/ion removal unnecessary.

After EDI unit 30, ions and/or fluids can be replaced in the clean fluid stream through the addition of one or more concentrated dialysis components from a concentrate or fluid metering source 80 via flow path 82. The concentrated dialysis components can include one or more osmotic agents (e.g., dextrose, icodextrin, glucose polymers, glucose polymer derivatives, amino acids), buffers (e.g., lactate, bicarbonate) and electrolytes (e.g. sodium, potassium, calcium, magnesium) from a small fluid source. After this addition, the fluid is compositionally equivalent to fresh dialysis solution and can be used to remove additional uremic toxins from the individual's blood stream.

To further realize the benefits of EDI over existing sorbent systems, EDI unit 30 would not be expected to be replaced over the foreseeable lifetime of the hemodialysis systems/devices. Carbon source 40 and urease source 50 can be replaced at some determined interval, but these are much lower cost components than sorbent cartridges and do not negatively impact the economic benefits of the system.

In an embodiment shown in FIG. 1, additions can be made to enhance the functionality and/or safety of the system. For example, biological purity of system 10 can be assured through replacement of circuits 12 and 14 after each treatment, along with dialyzer 20. However, circuits 12 and 14 can also be re-used for multiple treatments if suitable disinfection and sanitization methods were undertaken. These can include all currently accepted methods, such as heat sanitization, chemical sanitization (including ozonation), addition of ultraviolet ("UV") bactericidal lights, and the addition of additional dialyzers and/or ultrafilters in the system with a pore size appropriate for the removal of bacterial and sub-bacterial contaminants.

The monitoring of system 10 can be enhanced through the inclusion of an optional ammonia sensor in the loop after EDI unit 30 to ensure that all ammonia has been removed. Because fluid of resistance approaching 5 MΩ·cm can be made after passing through EDI unit 30, an optional conductivity sensor may be used to assure there is no ammonia versus the traditional approach of using an ammonia sensor. Finally, one or more optional ion exchanger unit 60 that have low cost and/or high capacity can be used to supplement EDI unit 30 to improve its performance or reduce its necessary size. These optional ion exchangers can include a phosphate removal exchanger with a bicarbonate counter ion to enhance phosphate removal or a cation exchanger that helps to remove any remaining ammonia.

The dialyzers in any embodiments of the present disclosure can include an ion-rejection membrane that allows the passage of negatively charged ions and nonionic species but restricts the passage of positively charged ions. Alternatively, the dialyzers in any embodiments of the present disclosure can include an ion-rejection membrane that allows the passage of positively charged ions and nonionic species but restricts the passage of negatively charged ions.

Figure 2:
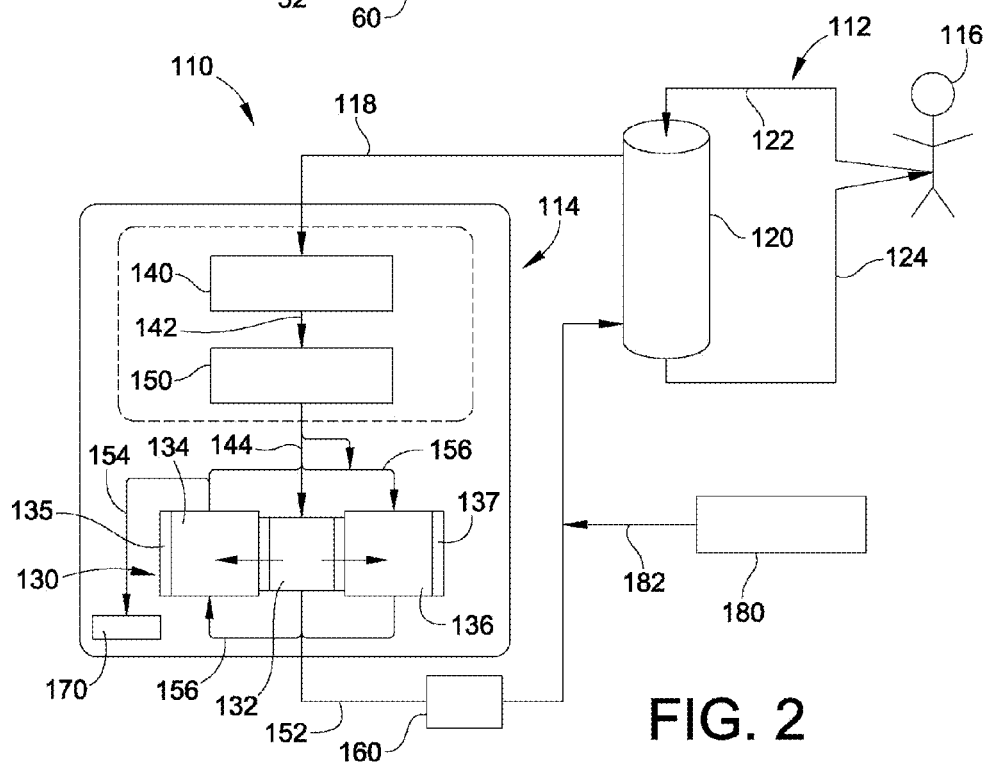
FIG. 2 illustrates a schematic of a dialysis fluid recycling system for peritoneal dialysis in an embodiment of the present disclosure.

In another embodiment, a dialysis fluid recycling system 110 for peritoneal dialysis is illustrated in FIG. 2. As shown in FIG. 2, a circuit 112 cycles spent dialysis fluid from an individual 116 via flow path 122 through a dialyzer 120 and returns it to the individual's body via flow path 124. Dialyzer 120 can include a dialysate compartment and a peritoneal dialysis fluid compartment separated by a suitable membrane. A circuit 114 includes an EDI unit 130 in the dialysis fluid recycling system. Fluid from dialyzer 120 transfers to circuit 114 via flow path 118.

Circuit 114 can also include a carbon source 140 and a urease source 150 connected to carbon source 140 via flow path 142. Circuit 114 can further include an optional ion exchange unit 160 in fluid connection with EDI unit 130 via flow path 152. Flow path 152 can lead directly back to dialyzer 120. Carbon source 140, urease source 150 and/or ion exchange unit 160 can be in the form of removable cartridges.

EDI unit 130 can include a central chamber 132, an anion chamber 134 having an anode 135, and a cation chamber 136 having a cathode 137. As fluid flows through central chamber 132 via flow path 144, a potential difference between anode 135 and cathode 137 causes the electrolytes in the fluid in central chamber to flow into anion chamber 134 and cation chamber 136. The treated fluid that passes through EDI unit 130 exits as part of a treated fluid stream 152 that leads back to dialyzer 120. A waste fluid stream filled with electrolytes exits via flow path 54 that leads to a drain 170.

EDI unit 130 can also be modified so that a suitable quantity of fluid can be recirculated around EDI unit 130 via flow path 156. This reduces the amount of fluid flowing through EDI unit 130 that would end up as part of the waste fluid stream.

System 110 is nearly identical to the hemodialysis system 10 of FIG. 1. However, in this embodiment, the solution being passed through circuit 112 represents peritoneal dialysis fluid, rather than individual's 116 own blood. The peritoneal dialysis procedure can be run, for example, in a "continuous flow" mode, where used dialysis fluid exits the individual's peritoneum as new fluid enters it through a dual lumen catheter. The used fluid is passed through dialyzer 120 where uremic toxins are removed and the waste fluid is treated just as it would be in hemodialysis. The composition of a concentrate addition to the fluid stream in flow path 152 from a concentrate or fluid metering source 180 via flow path 182 may be specifically tailored for peritoneal dialysis.

Additions to this type of system, along with those described for the hemodialysis system, can be included to enhance effectiveness or safety of the system. In an embodiment, the typical dialyzer membrane can be replaced with an ion-rejection membrane that allows the passage of negatively charged ions and nonionic species, but restricts the passage of positively charged ions (or vice versa). In this case, the peritoneal dialysis loop that is recirculating to the individual would be cleared of uremic toxins (which are neutrally or negatively charged), but the concentrate addition would not need to include replacement of the positive ions of the dialysis solution, which enhances the efficiency of the system.

Figure 3:
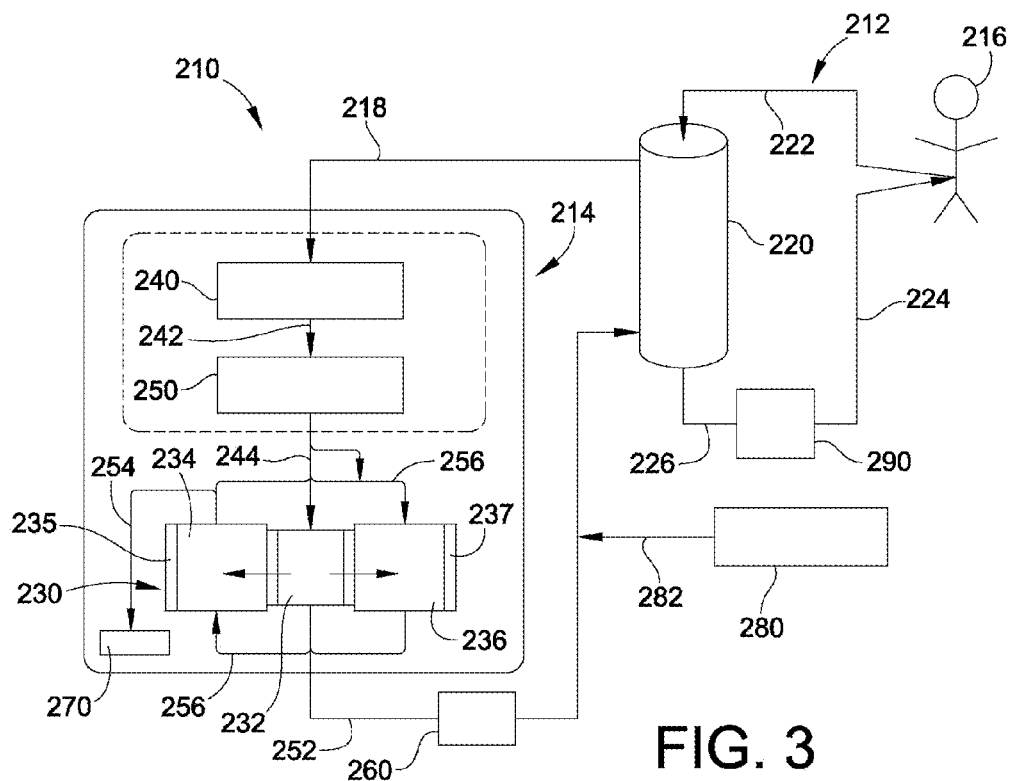
FIG. 3 illustrates a schematic of a dialysis fluid recycling system in another embodiment of the present disclosure.

In an alternative embodiment, a dialysis fluid recycling system 210 for hemodialysis or peritoneal dialysis is illustrated in FIG. 3. As shown in FIG. 3, a circuit 212 cycles fluid from an individual 216 through a dialyzer 220 and returns it to the individual's body. A circuit 214 includes an EDI unit or module 230 in the dialysis fluid recycling system.

Circuit 214 can also include a carbon source 240 and a urease source 250 connected to carbon source 240 via flow path 242. Circuit 214 can further include an optional ion exchange unit 260 in fluid connection with EDI unit 230 via flow path 252. Flow path 252 can lead directly back to dialyzer 220. Carbon source 240, urease source 250 and/or ion exchange unit 260 can be in the form of removable cartridges.

EDI unit 230 can include a central chamber 232, an anion chamber 234 having an anode 235, and a cation chamber 236 having a cathode 237. As fluid flows through central chamber 232 via flow path 244, a potential difference between anode 235 and cathode 237 causes the electrolytes in the fluid in central chamber to flow into anion chamber 234 and cation chamber 236. The treated fluid that passes through EDI unit 230 exits as part of a treated fluid stream 252. A waste fluid stream filled with electrolytes exits via flow path 254 that leads to a drain 270.

EDI unit 230 can also be modified so that a suitable quantity of fluid can be recirculated around EDI unit 230 via flow path 256. This reduces the amount of fluid flowing through EDI unit 230 that would end up as part of the waste fluid stream.

After leaving EDI unit 230 via flow path 252, one or more dialysis components from a concentrate or fluid metering source 280 via flow path 282 may be specifically tailored for the specific type of dialysis performed. An additional purification or treatment component 290 in the form of a filter or ultraviolet bactericidal light can be added to circuit 212, as shown in FIG. 3. Fluid exiting dialyzer 220 via flow path 226 can be further filtered or subject to a bactericidal light to enhance the bacterial purity of system 210. The treated fluid can then enter individual 216 via flow path 224. Purification component 290 can be especially important to peritoneal dialysis because bacterial contamination is a significant concern for the treatment.

Figure 4:
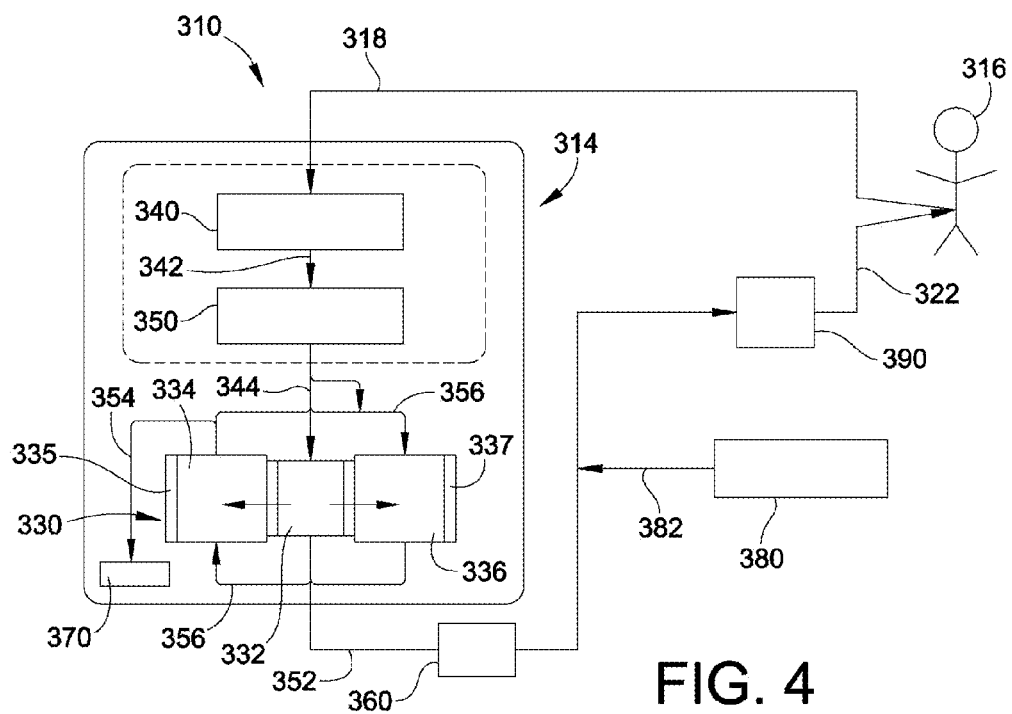
FIG. 4 illustrates a schematic of a dialysis fluid recycling system for peritoneal dialysis in an embodiment of the present disclosure.

In yet another embodiment, a dialysis fluid recycling system 310 for peritoneal dialysis is illustrated in FIG. 4. As shown in FIG. 4, a circuit 312 cycles blood from an individual 316 through a circuit 314. In order to perform the peritoneal dialysis treatment as shown in FIG. 4, flow path 318 of recycling system 310 can be constructed such that spent dialysis fluid from individual 316 is sent directly to recycling system 310 without the need for "dialyzing" the PD fluid. The peritoneal dialysis procedure can be run, for example, in a "continuous flow" mode.

Circuit 314 includes an EDI unit or module 330 in the dialysis fluid recycling system. Circuit 314 can also include a carbon source 340 and a urease source 350 connected to carbon source 340 via flow path 342. Circuit 314 can further include an optional ion exchange unit 360 in fluid connection with EDI unit 330 via flow path 352. Flow path 352 can lead directly back to dialyzer 320. Carbon source 340, urease source 350 and/or ion exchange unit 360 can be in the form of removable cartridges.

EDI unit 330 can include a central chamber 332, an anion chamber 334 having an anode 335, and a cation chamber 336 having a cathode 337. As fluid flows through central chamber 332 via flow path 344, a potential difference between anode 335 and cathode 337 causes the electrolytes in the fluid in central chamber to flow into anion chamber 334 and cation chamber 336. The treated fluid that passes through EDI unit 330 exits as part of a treated fluid stream 352. A waste fluid stream filled with electrolytes exits via flow path 354 that leads to a drain 370.

EDI unit 330 can also be modified so that a suitable quantity of fluid can be recirculated around EDI unit 330 via flow path 356. This reduces the amount of fluid flowing through EDI unit 330 that would end up as part of the waste fluid stream.

After leaving EDI unit 330 via flow path 352, one or more dialysis components from a concentrate or fluid metering source 380 via flow path 382 may be specifically tailored for the type of dialysis performed. An additional purifying component 390 such as a filter, UV light, and/or other commonly accepted methods can optionally be used on the inlet line to the individual's 316 peritoneal cavity to prevent bacterial contamination and also on the line from the individual back to system 310 (not shown) to prevent retro-contamination to individual 316. The purified dialysis solution can be provided to individual 316 via flow path 322.

Figure 5:
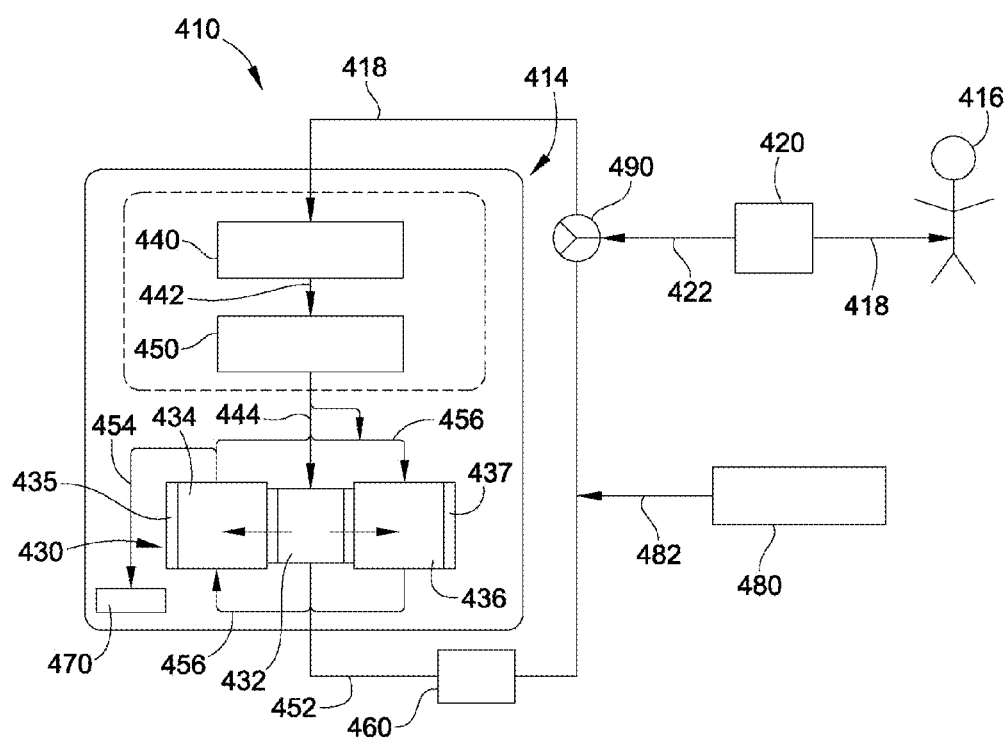
FIG. 5 illustrates a schematic of a dialysis fluid recycling system for peritoneal dialysis in another embodiment of the present disclosure.

In yet another embodiment, a dialysis fluid recycling system 410 for peritoneal dialysis is illustrated in FIG. 5. As shown in FIG. 5, a circuit 412 cycles dialysis fluid from an individual 416 to via flow path 422 to a three way valve 490. From three-way valve 490, the fluid flows to a circuit 414 via flow path 418 where the fluid is recycled. System 410 is designed to operate in a standard peritoneal dialysis therapy mode where fluid is injected, allowed to dwell, then removed from individual 416. Once the dialysis fluid has been purified, the dialysis fluid is then sent back to individual 416 via flow path 418, allowed to dwell, removed, purified, and repeated. The control of the flow direction can be accomplished with three-way valve 490 as shown in FIG. 5.

Circuit 414 includes an EDI unit 430. Circuit 414 can also include a carbon source 440 and a urease source 450 connected to carbon source 440 via flow path 442. Circuit 414 can further include an optional ion exchange unit 460 in fluid connection with EDI unit 430 via flow path 452. Flow path 552 can lead directly back to dialyzer 420. Carbon source 440, urease source 450 and/or ion exchange unit 460 can be in the form of removable cartridges. After leaving EDI unit 430 via flow path 452, one or more dialysis components from a concentrate or fluid metering source 480 via flow path 482 may be specifically tailored for the type of dialysis performed.

EDI unit 430 can include a central chamber 432, an anion chamber 434 having an anode 435, and a cation chamber 436 having a cathode 437. As fluid flows through central chamber 432 via flow path 444, a potential difference between anode 435 and cathode 437 causes the electrolytes in the fluid in central chamber to flow into anion chamber 434 and cation chamber 436. The treated fluid that passes through EDI unit 430 exits as part of a treated fluid stream 452. A waste fluid stream filled with electrolytes exits via flow path 454 that leads to a drain 470.

EDI unit 430 can also be modified so that a suitable quantity of fluid can be recirculated around EDI unit 430 via flow path 456. This reduces the amount of fluid flowing through EDI unit 430 that would end up as part of the waste fluid stream.

In addition to the modifications described herein, the dialysis fluid recycling systems can be further enhanced in several ways. First, the dialysis fluid recycling system can remove nearly all solutes from the used or spent dialysis solution (including therapeutically beneficial solutes, which would then need to be re-added). The dialysis fluid recycling system can also be designed to allow reduced removal of the active osmotic agent in the peritoneal dialysis fluid (e.g., glucose or dextrose). The osmotic reagent can be replaced with a longer acting molecule, such as glucose microspheres that can be reintroduced into the dialysis fluid, to maintain the osmotic gradient in the individual.

EXAMPLES

By way of example and not limitation, the following example is illustrative of an embodiment of the present disclosure.

Example 1

Experiments to determine the extent of the electrolyte removal using an EDI unit were performed. The experiments simulated EDI treatment of a post-urease dialysate. A peritoneal dialysis solution was spiked with 3200 ppm of Ammonium Carbonate (2000 ppm of urea can be converted into 3200 ppm of ammonium carbonate by urease). In different studies, the dialysis solution was passed through the EDI unit at a flow rate of 100 mL/min and 200 mL/min.

A Millipore EDI-15 Cell with a PK Precision VSP-12010 DC power supply was used as the EDI unit. Conductivity of the dialysis solution was measured using an Amber Science EC3084 Conductivity Meter.

Figure 6:
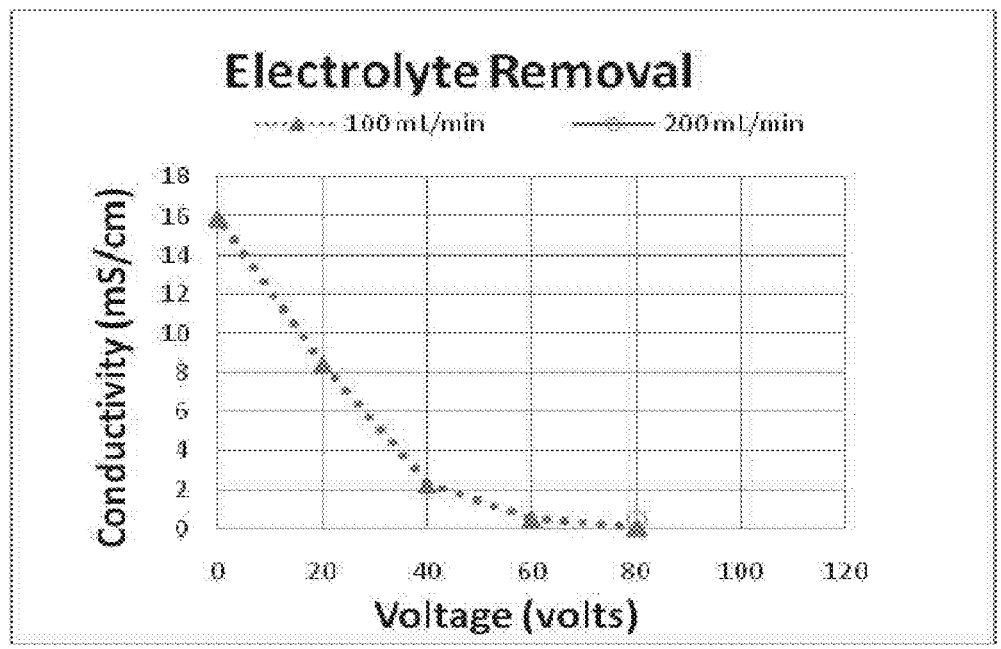
FIG. 6 is a graph showing the conductivity of a dialysis solution treated using an EDI unit versus the operating voltage of the EDI unit.
Figure 7:
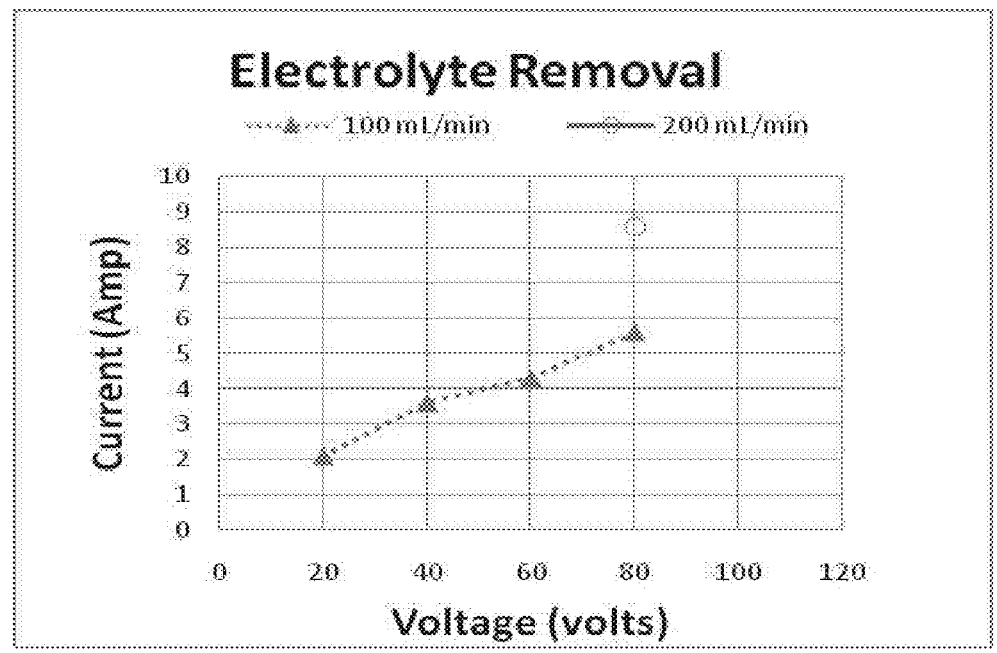
FIG. 7 is a graph showing the operating current of an EDI unit versus the operating voltage of the EDI unit.

During the experiments, the conductivity of the treated dialysis solution versus corresponding voltage/current of the EDI unit was measured. The final conductivity was compared to the original conductivity of the untreated dialysis solution. A summary of the results is shown in Table 1 and FIGS. 6 and 7. FIG. 6 shows the conductivity of a dialysis solution treated using the EDI unit versus the operating voltage of the EDI unit. FIG. 7 shows the operating current of the EDI unit versus the operating voltage of the EDI unit.

TABLE 1

| Dialysate flow rate (mL/min) | Voltage (Volts) | Current (Ampere) | Conductivity (mS/cm) | % Removal |
|---|---|---|---|---|
| 100 | 0 | 0 | 15.9 | 0 |
| 100 | 20 | 2.1 | 8.4 | 47 |
| 100 | 40 | 3.6 | 2.28 | 86 |
| 100 | 60 | 4.3 | 0.48 | 97 |
| 100 | 80 | 5.6 | 0.08 | 99 |
| 200 | 80 | 8.6 | 0.44 | 97 |

As show in Table 1 and FIGS. 6 and 7, a 99% electrolyte removal from the dialysis solution can be achieved using the EDI unit. It was also found that the EDI unit can be operated at a reduced voltage and reduced current to allow a specific percentage of electrolytes to pass through. This could allow the use of a smaller size EDI unit for better portability. In this case, the small amount of residue electrolytes, including ammonium ions, can be removed by a supplemental ion-exchange resin column down stream from the EDI unit.

Aspects of the subject matter described herein may be useful alone or in combination one or more other aspect described herein. Without limiting the foregoing description, in a first aspect of the present disclosure, a dialysis fluid recycling system includes: a carbon source; a urease source in fluid communication with the carbon source; and an electrodeionization unit in fluid communication with the urease source.

In accordance with a second aspect of the present disclosure, which may be used in combination with the first aspect, the dialysis fluid recycling system includes an ion exchange unit in fluid communication with the electrodeionization unit.

In accordance with a third aspect of the present disclosure, which may be used in combination with any one or more of the preceding aspects, the dialysis fluid recycling system includes a metering source in fluid communication with the electrodeionization unit.

In accordance with a fourth aspect of the present disclosure, which may be used in combination with any one or more of the preceding aspects, a hemodialysis system includes: a carbon source; a urease source in fluid communication with the carbon source; an electrodeionization unit in fluid communication with the urease source; and a dialyzer in fluid communication with the electrodeionization unit.

In accordance with a fifth aspect of the present disclosure, which may be used with any one or more of the preceding aspects in combination with the 4 aspect, the hemodialysis system includes an ion exchange unit in fluid communication with the dialyzer.

In accordance with a sixth aspect of the present disclosure, which may be used with any one or more of the preceding aspects in combination with the 4 aspect, the hemodialysis system includes a metering source in fluid communication with the dialyzer.

In accordance with a seventh aspect of the present disclosure, which may be used with any one or more of the preceding aspects in combination with the 4 aspect, the hemodialysis system includes a filter in fluid communication with the dialyzer.

In accordance with an eighth aspect of the present disclosure, which may be used with any one or more of the preceding aspects in combination with the 4 aspect, the hemodialysis system includes an ultraviolet bactericidal light in fluid communication with the dialyzer.

In accordance with a ninth aspect of the present disclosure, which may be used in combination with any one or more of aspects 1 to 3, a peritoneal dialysis system includes: a carbon source; a urease source in fluid communication with the carbon source; and an electrodeionization unit in fluid communication with the urease source.

In accordance with a tenth aspect of the present disclosure, which may be used with any one or more of aspects 1 to 3 in combination with aspect 9, the peritoneal dialysis system includes an ion exchange unit in fluid communication with the electrodeionization unit.

In accordance with an eleventh aspect of the present disclosure, which may be used with any one or more of aspects 1 to 3 in combination with aspect 9, the peritoneal dialysis system of claim 9, which includes a metering source in fluid communication with the electrodeionization unit.

In accordance with a twelfth aspect of the present disclosure, which may be used with any one or more of aspects 1 to 3 in combination with aspect 9, the peritoneal dialysis system of claim 9, which includes a filter in fluid communication with the electrodeionization unit.

In accordance with a thirteenth aspect of the present disclosure, which may be used with any one or more of aspects 1 to 3 in combination with aspect 9, the peritoneal dialysis system includes an ultraviolet bactericidal light in fluid communication with the electrodeionization unit.

In accordance with a fourteenth aspect of the present disclosure, which may be used in combination with any one or more of aspects 1 to 8, a method of performing hemodialysis includes: passing a spent dialysis fluid from a dialyzer through a carbon source, a urease source and an electrodeionization unit to produce a clean dialysis fluid; and passing the clean dialysis fluid through the dialyzer.

In accordance with a fifteenth aspect of the present disclosure, which may be used with any one or more of aspects 1 to 8 in combination with aspect 14, the method includes passing the clean dialysis fluid through an ion exchange unit before the clean dialysis fluid passes through the dialyzer.

In accordance with a sixteenth aspect of the present disclosure, which may be used with any one or more of aspects 1 to 8 in combination with aspect 14, the method includes adding at least one dialysis component to the clean dialysis fluid before the clean dialysis fluid passes through the dialyzer.

In accordance with a seventeenth aspect of the present disclosure, which may be used in combination with any one or more of aspects 1 to 3 and 9 to 13, a method of performing peritoneal dialysis includes: passing a spent dialysis fluid from an individual through a carbon source, a urease source and an electrodeionization unit to produce a clean dialysis fluid; and returning the clean dialysis fluid to the individual.

In accordance with an eighteenth aspect of the present disclosure, which may be used with any one or more of aspects 1 to 3 and 9 to 13 in combination with aspect 17, the method includes passing the clean dialysis fluid through an ion exchange unit before the clean dialysis fluid returns to the patient.

In accordance with a nineteenth aspect of the present disclosure, which may be used with any one or more of aspects 1 to 3 and 9 to 13 in combination with aspect 17, the method includes adding at least one dialysis component to the clean dialysis fluid before the clean dialysis fluid returns to the individual.

In accordance with a twentieth aspect of the present disclosure, which may be used with any one or more of aspects 1 to 3 and 9 to 13 in combination with aspect 17, the method includes passing the clean dialysis fluid through a filter before the clean dialysis fluid returns to the patient.

In accordance with a twenty-first aspect of the present disclosure, which may be used with any one or more of aspects 1 to 3 and 9 to 13 in combination with aspect 17, the method includes passing the clean dialysis fluid through an ultraviolet bactericidal light before the clean dialysis fluid returns to the patient.

In accordance with a twenty-second aspect of the present disclosure, which may be used in combination with any one or more of the preceding aspects, a method of performing dialysis includes: passing a spent dialysis fluid through a dialysis compartment of a dialyzer including an ion-rejection membrane that allows the passage of negatively charged ions and nonionic species but restricts the passage of positively charged ions, the ion-rejection membrane separating the dialysis compartment from a dialysate compartment of the dialyzer; passing used dialysis fluid generated from the dialysate compartment of the dialyzer through a carbon source, a urease source and an electrodeionization unit to produce a clean dialysis fluid; adding a source of negative ions to the clean dialysis fluid; and passing the clean dialysis fluid through the dialysate compartment of the dialyzer.

In accordance with a twenty-fourth aspect of the present disclosure, which may be used in combination with any one or more of the preceding aspects, a method of performing dialysis includes: passing a spent dialysis fluid through a dialysis compartment of a dialyzer including an ion-rejection membrane that allows the passage of positively charged ions and nonionic species but restricts the passage of negatively charged ions, the ion-rejection membrane separating the dialysis compartment from a dialysate compartment of the dialyzer; passing used dialysis fluid generated from the dialysate compartment of the dialyzer through a carbon source, a urease source and an electrodeionization unit to produce a clean dialysis fluid; adding a source of positive ions to the clean dialysis fluid; and passing the clean dialysis fluid through the dialysate compartment of the dialyzer.

In accordance with a twenty-fifth aspect of the present disclosure, any of the structure and functionality illustrated and described in connection with FIG. 1 may be used in combination with any one or more of the preceding hemodialysis aspects.

In accordance with a twenty-sixth aspect of the present disclosure, any of the structure and functionality illustrated and described in connection with FIG. 2 may be used in combination with any one or more of the preceding peritoneal dialysis aspects.

In accordance with a twenty-seventh aspect of the present disclosure, any of the structure and functionality illustrated and described in connection with FIG. 3 may be used in combination with any one or more of the preceding aspects.

In accordance with a twenty-eighth aspect of the present disclosure, any of the structure and functionality illustrated and described in connection with FIG. 4 may be used in combination with any one or more of the preceding peritoneal dialysis aspects.

In accordance with a twenty-ninth aspect of the present disclosure, any of the structure and functionality illustrated and described in connection with FIG. 5 may be used in combination with any one or more of the preceding peritoneal dialysis aspects.

In accordance with a thirtieth aspect of the present disclosure, any of the structure and functionality illustrated and described in connection with FIG. 6 may be used in combination with any one or more of the preceding aspects.

In accordance with a thirty-first aspect of the present disclosure, any of the structure and functionality illustrated and described in connection with FIG. 7 may be used in combination with any one or more of the preceding aspects.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A portable dialysis fluid recycling system comprising:
a carbon source;
a urease source in fluid communication with the carbon source;
an electrodeionization unit in fluid communication with the urease source;
an ammonia sensor in fluid communication with the electrodeionization unit; and
an ion exchange unit in fluid communication with the electrodeionization unit, wherein at least one of the carbon source, the urease source and the ion exchange unit is provided in a removable cartridge.

2. The portable dialysis fluid recycling system of claim 1, wherein the ammonia sensor is a conductivity sensor.

3. The portable dialysis fluid recycling system of claim 1, which includes a metering source in fluid communication with the electrodeionization unit.

4. A portable hemodialysis system comprising:
a carbon source;
a urease source in fluid communication with the carbon source;
an electrodeionization unit in fluid communication with the urease source;
an ammonia sensor in fluid communication with the electrodeionization unit;
an ion exchange unit in fluid communication with the electrodeionization unit; and
a dialyzer in fluid communication with the electrodeionization unit,
wherein at least one of the carbon source, the urease source and the ion exchange unit is provided in a removable cartridge.

5. The portable hemodialysis system of claim 4, wherein the ammonia sensor is a conductivity sensor.

6. The portable hemodialysis system of claim 4, which includes a metering source in fluid communication with the dialyzer.

7. The portable hemodialysis system of claim 4, which includes a filter in fluid communication with the dialyzer.

8. The portable hemodialysis system of claim 4, which includes an ultraviolet bactericidal light in fluid communication with the dialyzer.

9. A portable peritoneal dialysis system comprising:
a carbon source;
a urease source in fluid communication with the carbon source; and
an electrodeionization unit in fluid communication with the urease source;
an ammonia sensor in fluid communication with the electrodeionization unit; and
an ion exchange unit in fluid communication with the electrodeionization unit, wherein at least one of the carbon source, the urease source and the ion exchange unit is provided in a removable cartridge.

10. The portable peritoneal dialysis system of claim 9, wherein the ammonia sensor is a conductivity sensor.

11. The portable peritoneal dialysis system of claim 9, which includes a metering source in fluid communication with the electrodeionization unit.

12. The portable peritoneal dialysis system of claim 9, which includes a filter in fluid communication with the electrodeionization unit.

13. The portable peritoneal dialysis system of claim 9, which includes an ultraviolet bactericidal light in fluid communication with the electrodeionization unit.

14. The portable dialysis fluid recycling system of claim 1, wherein the electrodeionization unit includes a central chamber, an anion chamber having an anode, and a cation chamber having a cathode.

15. The portable dialysis fluid recycling system of claim 1, wherein the electrodeionization unit is configured such that a quantity of fluid can be recirculated around the electrodeionization unit via a flow path.

16. The portable dialysis fluid recycling system of claim 1, wherein the carbon source and the urease source are each provided in the same removable cartridge.

17. The portable hemodialysis system of claim 4, wherein the electrodeionization unit includes a central chamber, an anion chamber having an anode, and a cation chamber having a cathode.

18. The portable hemodialysis system of claim 4, wherein the electrodeionization unit is configured such that a quantity of fluid can be recirculated around the electrodeionization unit via a flow path.

19. The portable hemodialysis system of claim 4, wherein the carbon source and the urease source are each provided in the same removable cartridge.

20. The portable peritoneal dialysis system of claim 9, wherein the electrodeionization unit includes a central chamber, an anion chamber having an anode, and a cation chamber having a cathode.

21. The portable peritoneal dialysis system of claim 9, wherein the electrodeionization unit is configured such that a quantity of fluid can be recirculated around the electrodeionization unit via a flow path.

22. The portable peritoneal dialysis system of claim 9, wherein the carbon source and the urease source are each provided in the same removable cartridge.

* * * * *